(12) United States Patent
Wilson et al.

(10) Patent No.: US 7,381,204 B2
(45) Date of Patent: Jun. 3, 2008

(54) MULTI-LUMEN CATHETER WITH ATTACHABLE HUB

(75) Inventors: Jon S. Wilson, Winston-Salem, NC (US); Carl M. Fleming, Palm City, FL (US); Kenneth T. Cassidy, Mocksville, NC (US); Ronald D. Boyd, Statesboro, GA (US); Gary S. Fleming, Palm City, FL (US)

(73) Assignee: Arrow International, Inc., Reading, PA (US)

( * ) Notice: Subject to any disclaimer, the term of this patent is extended or adjusted under 35 U.S.C. 154(b) by 659 days.

(21) Appl. No.: 10/612,532

(22) Filed: Jul. 1, 2003

(65) Prior Publication Data

US 2004/0065333 A1    Apr. 8, 2004

Related U.S. Application Data

(63) Continuation of application No. 10/086,033, filed on Feb. 28, 2002, now Pat. No. 6,638,242, which is a continuation of application No. 09/769,052, filed on Jan. 24, 2001, now abandoned.

(51) Int. Cl.
*A61M 31/00* (2006.01)
(52) U.S. Cl. ...................... 604/500; 128/898
(58) Field of Classification Search .................. 604/43, 604/500, 506–508, 264, 523, 533–539, 284; 128/898
See application file for complete search history.

(56) References Cited

U.S. PATENT DOCUMENTS 4,134,402 A    1/1979 Mahurkar (Continued)

FOREIGN PATENT DOCUMENTS

EP    0 321 648    6/1988

(Continued)

OTHER PUBLICATIONS

Instructions for Use (Copyright Dated 1990) for Polycath Polyurethane Central Venous Catheter; believed to have been packaged with product believed to have been sold in the United States before Jan. 2000 and related marketing materials.

(Continued)

*Primary Examiner*—Nicholas D. Lucchesi
*Assistant Examiner*—Christopher D Koharski
(74) *Attorney, Agent, or Firm*—Amster Rothstein & Ebenstein LLP

(57) ABSTRACT

A method of inserting a multi-lumen catheter assembly. First, an incision is made near the area to be catheterized. The proximal portion of the multi-lumen catheter tube is then inserted into the area to be catheterized. A subcutaneous tunnel is created, and the first end of the tunnel is near the incision. The catheter tube is then routed through the subcutaneous tunnel and pulled tube through a second end of the subcutaneous tunnel. The hub body is then securely attached to the catheter tube by connecting the connection cover to the hub body by threaded engagement. In a preferred embodiment the hub body is attached to the catheter tube by backfitting the connection cover over the catheter tube. A compression sleeve is also backfit over the catheter tube. The cannulae of the hub body are inserted into the lumens of the catheter tube to create fluid communication therebetween. The connection between the cannulae and the first and the catheter tube is compressed by sliding the compression sleeve over the cannulae that have been inserted into the catheter tube.

15 Claims, 7 Drawing Sheets

U.S. PATENT DOCUMENTS

| | | | | |
|---|---|---|---|---|
| 4,299,228 | A | 11/1981 | Peters | 604/122 |
| 4,327,722 | A | 5/1982 | Grosborg | 604/510 |
| 4,432,752 | A | 2/1984 | Marlon | 604/500 |
| 4,453,928 | A | 6/1984 | Steiger | 604/500 |
| RE31,873 | E | 4/1985 | Howes | |
| 4,543,087 | A | 9/1985 | Sommercorn et al. | |
| 4,568,329 | A | 2/1986 | Mahurkar | |
| 4,619,643 | A | 10/1986 | Bai | |
| 4,623,327 | A | 11/1986 | Mahurkar | |
| 4,643,711 | A | 2/1987 | Bates | |
| 4,675,004 | A | 6/1987 | Hadford et al. | |
| 4,681,122 | A | 7/1987 | Winters et al. | |
| 4,682,978 | A | 7/1987 | Martin | 604/43 |
| 4,692,141 | A | 9/1987 | Mahurkar | |
| 4,713,171 | A | 12/1987 | Polaschegg | |
| 4,772,268 | A | 9/1988 | Bates | |
| 4,772,269 | A | 9/1988 | Twardowski | 604/175 |
| 4,808,155 | A | 2/1989 | Mahurkar | |
| 4,832,687 | A | 5/1989 | Smith, III | 604/506 |
| 4,895,561 | A | 1/1990 | Mahurkar | |
| 5,053,003 | A | 10/1991 | Dadson et al. | |
| 5,053,004 | A | 10/1991 | Markel et al. | |
| 5,053,023 | A | 10/1991 | Martin | |
| 5,059,170 | A | 10/1991 | Cameron | |
| 5,106,368 | A | 4/1992 | Uldall et al. | 604/43 |
| 5,129,891 | A | 7/1992 | Young | |
| 5,171,227 | A | 12/1992 | Twardowski | 604/175 |
| 5,190,520 | A | 3/1993 | Fenton, Jr. et al. | |
| 5,221,255 | A * | 6/1993 | Mahurkar et al. | 604/43 |
| 5,312,337 | A | 5/1994 | Flaherty et al. | |
| 5,322,519 | A | 6/1994 | Ash | |
| 5,334,185 | A | 8/1994 | Giesy et al. | |
| 5,342,386 | A | 8/1994 | Trotta | |
| 5,360,397 | A | 11/1994 | Pinchuk | |
| 5,380,276 | A | 1/1995 | Miller et al. | |
| 5,399,168 | A | 3/1995 | Wadsworth, Jr. et al. | |
| 5,405,320 | A | 4/1995 | Twardowski et al. | |
| 5,405,341 | A | 4/1995 | Martin | |
| 5,417,668 | A | 5/1995 | Setzer et al. | |
| 5,423,768 | A | 6/1995 | Folder | 604/200 |
| 5,431,661 | A | 7/1995 | Koch | |
| 5,472,432 | A | 12/1995 | Martin | |
| 5,509,897 | A | 4/1996 | Twardowski et al. | |
| 5,558,635 | A | 9/1996 | Cannon | |
| 5,599,328 | A | 2/1997 | Stevens | 604/280 |
| 5,624,413 | A | 4/1997 | Market et al. | |
| 5,632,729 | A | 5/1997 | Cai et al. | |
| 5,637,102 | A | 6/1997 | Tolkoff et al. | |
| 5,685,867 | A | 11/1997 | Twardowski | 604/523 |
| 5,704,915 | A | 1/1998 | Melsky et al. | |
| 5,718,678 | A | 2/1998 | Fleming, III | |
| 5,718,692 | A | 2/1998 | Schon et al. | |
| 5,743,873 | A | 4/1998 | Cai et al. | |
| 5,772,643 | A | 6/1998 | Howell et al. | |
| 5,776,111 | A | 7/1998 | Tesio | |
| 5,797,869 | A | 8/1998 | Martin | |
| 5,807,311 | A | 9/1998 | Palestrant | |
| 5,876,366 | A | 3/1999 | Dykstra et al. | |
| 5,944,732 | A | 8/1999 | Raulerson et al. | |
| 5,947,937 | A | 9/1999 | Urrutia et al. | |
| 5,947,953 | A | 9/1999 | Ash et al. | 604/508 |
| 5,989,206 | A | 11/1999 | Prosl et al. | 604/501 |
| 5,989,213 | A | 11/1999 | Maginot | |
| 6,001,079 | A | 12/1999 | Pourchez | |
| 6,033,382 | A | 3/2000 | Basta | |
| 6,074,374 | A | 6/2000 | Fulton | |
| 6,086,555 | A | 7/2000 | Eliasen et al. | |
| 6,113,572 | A | 9/2000 | Gailey et al. | |
| 6,156,016 | A | 12/2000 | Maginot | |
| 6,190,349 | B1 | 2/2001 | Ash et al. | |
| 6,190,371 | B1 | 2/2001 | Maginot | |
| 6,206,849 | B1 | 3/2001 | Martin et al. | |
| 6,293,927 | B1 | 9/2001 | McGuckin, Jr. | |
| 6,322,551 | B1 | 11/2001 | Brugger | |
| 6,342,120 | B1 | 1/2002 | Basta | |
| 6,428,513 | B1 | 8/2002 | Abrahamson | |
| 6,585,705 | B1 | 7/2003 | Maginot et al. | 604/265 |
| 6,638,242 | B2 | 10/2003 | Wilson et al. | |
| 6,682,498 | B2 | 1/2004 | Ross | |
| 6,682,519 | B1 | 1/2004 | Schon | 604/508 |
| 6,719,749 | B1 | 4/2004 | Schweikert et al. | |
| 6,749,574 | B2 | 6/2004 | O'Keefe | |
| 6,858,019 | B2 | 2/2005 | McGuckin et al. | |
| 6,872,198 | B1 | 3/2005 | Wilson et al. | |
| 6,921,396 | B1 | 7/2005 | Wilson et al. | |
| 7,128,734 | B1 | 10/2006 | Wilson et al. | |
| 2001/0041857 | A1 | 11/2001 | Sansoucy | 604/33 |
| 2003/0088213 | A1 | 5/2003 | Schweikert et al. | 604/177 |
| 2003/0153898 | A1 | 8/2003 | Schon et al. | 604/544 |

FOREIGN PATENT DOCUMENTS

| | | |
|---|---|---|
| EP | 0 321 648 A1 | 8/1988 |
| WO | WO 98/08357 | 3/1995 |
| WO | WO97/22374 * | 6/1997 |
| WO | WO 9722374 | 6/1997 |

OTHER PUBLICATIONS

Instructions for Use (Copyright Dated 1992) for FloLock Single Lumen Bi-directional Valved Catheter; believed to have been packaged with product believed to have been sold in the United States before Jan. 2000.

Instructions for Use (not dated) for Infuse-a-Cath Polyurethane Central Venous Catheter; believed to have been packaged with product believed to have been sold in the United States before Jan. 2000.

Pictures of device believed to be partial sample of a product believed to have been sold in the United States before Jan. 2000 with the Polycath and/or Infuse-a-Cath Instructions for Use.

Copending U.S. Appl. No. 10/251,411; entitled Multi-Lumen Catheter with Attacheble Hub, filed Sep. 20, 2002.

Copending U.S. Appl. No. 10/231,577; entitled Multi-Lumen Catheter with Integrated Connector, filed Aug. 30, 2002.

Copending U.S. Appl. No. 10/231,748; Double Y-Shaped Multi-Lumen Catheter with Selectively Attachable Hubs, filed Aug. 30, 2002.

Abandoned U.S. Appl. No. 10/086,033; entitled Multi-Lumen Catheter with Attacheble Hub, filed Jan. 24, 2001.

Instructions For Use For Diatek Cannon Catheter Product First Sold in the United States Sep. 2001.

Twardowski, TJ, Opti-Flow Catheter Tip Translocation From the Right Atrium to the Right Ventrical, 2001; 2: pp. 17-19, Wichtig Editore, 2001.

Bio-Flex Tesio Catheters, Sales Brochure, Rev. D, Apr. 2006.

SCHON Chronic Dialysis Catheter, Sales Brochure, Rev. D, Apr. 2005.

Pourchez Retro and Pourchez Xpresso, Sales Brochure.

Response to Interrogatory No. 3 by Defendant Spire Biomedical, Inc. in the matter of Arrow International, Inc. et al. v. Spire Biomedical, Inc., Civil Action No.: 05-10671 (DPW) U.S. Dist. Ct. Dist. of Massachusetts.

Wheeler, R.A., et al., Retrograde Tunnel: A Method for the Fixation of Long-Term Pediatric Central Lumen Catheters, Journal of Parenteral and Enteral Nutrition, Jan.-Feb. 1991; pp. 114-115; vol. 14-No. 1, American Society for Parenteral and Enteral Nutrition, U.S.

Wheeler, R.A., et al., Retrograde Tunnel: A Method for the Fixation of Central Venous Catheters in the Military Environment, Journal of the Royal Navy Medical Service, Summer 1991; pp. 75-77; vol. 77, United Kingdom.

Pourchez Retro Instructions for Use.

Pourchez Xpresso Product Label dated Feb. 5, 2002.

Twardowski, Z.J., Vascular Access for Hemodialysis: A Historical Perspective for Intravenous Catheters, The Journal for Vascular Access, 2000, 1: 42-45, Wichtig Editore 2000.

COMPLAINT from Arrow International, Inc., et al. v. Spire Biomedical, Inc. asserting U.S. Patent No. 6,872,198 which shares common "Related U.S. Applications" with the present application, i.e. U.S. Appl. No. 10/086,033, now U.S. Patent No. 6,638,242 and U.S. Appl. No. 09/769,092, now abandoned.

Reexamination Office Action, dated Sep. 15, 2006, in Reexamination Control No. 09/007,072, which is an ex parte reexamination of U.S. Patent No. 6,638,242 of which the current application is a continuation.

Reexamination Office Action, dated Jul. 15, 2005, in Reexamination Control No. 09/007,072, which is an ex parte reexamination of U.S. Patent No. 6,638,242 of which the current application is a continuation.

* cited by examiner

MULTI-LUMEN CATHETER WITH ATTACHABLE HUB

RELATED APPLICATIONS

This application is a Continuation of application Ser. No. 10/086,033, filed Feb. 28, 2002, now U.S. Pat. No. 6,638,242, the content of which is incorporated herein by reference in its entirety, which was a continuation of application Ser. No. 09/769,052, filed Jan. 24, 2001, now abandoned.

FIELD OF THE INVENTION

The present invention relates generally to medical instrumentation and more specifically to a method for inserting a multi-lumen catheter with a selectively attachable hub assembly that allows the catheter tip to be accurately positioned prior to subcutaneous tunneling.

BACKGROUND OF THE INVENTION

Catheters, generally, are hollow, flexible tubes for insertion into a body cavity, duct, or vessel to allow the passage of fluids or distend a passageway. Catheters are often used for temporary or long-term dialysis treatment. Dialysis treatment provides for blood to be withdrawn from the patient, purified, and then returned to the patient. Thus, in dialysis treatment, catheters are used to allow passage of a patient's blood into and out of the patient's body. For optimal performance during dialysis treatment, the catheter tips, both in-flow and outflow, should be placed in close proximity to the heart. Typically, medical personnel use either a double lumen catheter or two single lumen catheters. Both types, however, present certain deficiencies.

While double lumen catheters (e.g., U.S. Pat. No. 4,895,561) allow for a single venous insertion of the catheter into the desired vein, double lumen catheters typically do not provide for accuracy of catheter tip placement. Due to differences among patients, optimal tip position varies from patient to patient. Non-optimal tip position may significantly lower flow values, resulting in less effective dialysis treatment. For current double lumen catheters, a physician must make an estimate regarding the appropriate catheter tube length prior to beginning the procedure of catheterization. Then, a subcutaneous tunnel is made from the preferred end position of the hub assembly, namely, away from the neck of the patient in order to allow for more convenient access to the dialysis treatment equipment. The double lumen catheter tube is then tunneled forwardly into the patient's vein. The initial estimate and subsequent forward tunneling may result in less than optimal tip placement.

With the use of two independent catheters (e.g., U.S. Pat. Nos. 5,776,111 and 5,624,413) the problem of tip placement is addressed. The hub assembly of each catheter is removable from the tube and tip portion of the catheter, thereby allowing the catheter tip to be placed directly into the vein and advanced into the desired position. Then, the proximal end of the catheter can be reversed tunneled and trimmed to a desired length. Thereafter, the hub assembly is attached. Deficiencies, however, exist in this method of catheterization as well. One problem associated with this method is that this method requires two separate venous insertions, namely, two tunnels and two of each accessory instrument used for the procedure. Therefore, there is increased surgical time required to place two catheters, there are two wound entry sites which doubles the risk of post-surgical infection, and the two catheters together are significantly larger in diameter than one double lumen catheter.

SUMMARY OF THE INVENTION

The present invention is a method for inserting a multi-lumen catheter assembly into an area to be catheterized The multi-lumen catheter assembly is comprised of (a) a multi-lumen catheter tube with a distal portion and a proximal portion, the catheter tube having a first lumen and a second lumen, (b) an attachable hub assembly, the hub assembly having a (i) a hub body with a distal portion and a proximal portion, the proximal portion of the hub body being externally threaded, the hub body being formed about a first cannula and a second cannula, each of the cannula having a proximal portion and a distal portion, (ii) a connection cover having a proximal portion and a distal portion, the connection cover fitting axially about the distal portion of the catheter tube, the distal portion of the connection cover being internally threaded, and (iii) a compression sleeve, the compression sleeve fitting axially about the distal portion of the catheter tube and the proximal portions of the first and second cannulae. The first lumen and the first cannula each have first indicator associated therewith, and the second lumen and the second cannula each have a second indicator associated therewith The method comprising the steps of making an incision near the area to be catheterized; inserting the proximal portion of the multi-lumen catheter tube into the area to be catheterized; creating a subcutaneous tunnel, wherein a first end of the subcutaneous tunnel is the incision near the area to be catheterized; routing the distal portion of the catheter tube through the subcutaneous tunnel beginning at the first end and exiting through a second end of the subcutaneous tunnel; and attaching the proximal portion of the hub body to the distal portion of the catheter tube.

The step of attaching the hub body to the catheter tube is further comprised of the steps of backfitting the connection cover over the distal portion of the catheter tube; backfitting the compression sleeve over the distal portion of the catheter tube; matching the first indicator associated with the first lumen with the first indicator associated with the first cannula, and inserting the proximal portion of the first cannula into the first lumen of the distal portion of the catheter tube, to create fluid communication between the first cannula and the first lumen; and matching the second indicator associated with the second lumen with the second indicator associated with the second cannula, and inserting the proximal portion of the second cannula into the second lumen of the distal portion of the catheter tube, to create fluid communication between the second cannula and the second lumen; compressing the connection between the first and second cannulae and the first and second lumens of the catheter tube by sliding the compression sleeve over the proximal portion of the first and second cannulae that have been inserted into the first and second lumens of the distal portion of the catheter tube, and connecting the distal portion of the connection cover to the proximal portion of the hub body by turning the connection cover so that the female threaded portion of the connection cover engages the male threaded portion of the hub body, such that the catheter tube is securely attached to the hub body.

These and other aspects of the present invention as disclosed herein will become apparent to those skilled in the art after a reading of the following description of the preferred embodiments and drawings. The description and drawings are for the purpose of describing a preferred embodiment of the invention and are not intended to limit the present invention.

DESCRIPTION OF THE PREFERRED EMBODIMENTS

Figure 1:
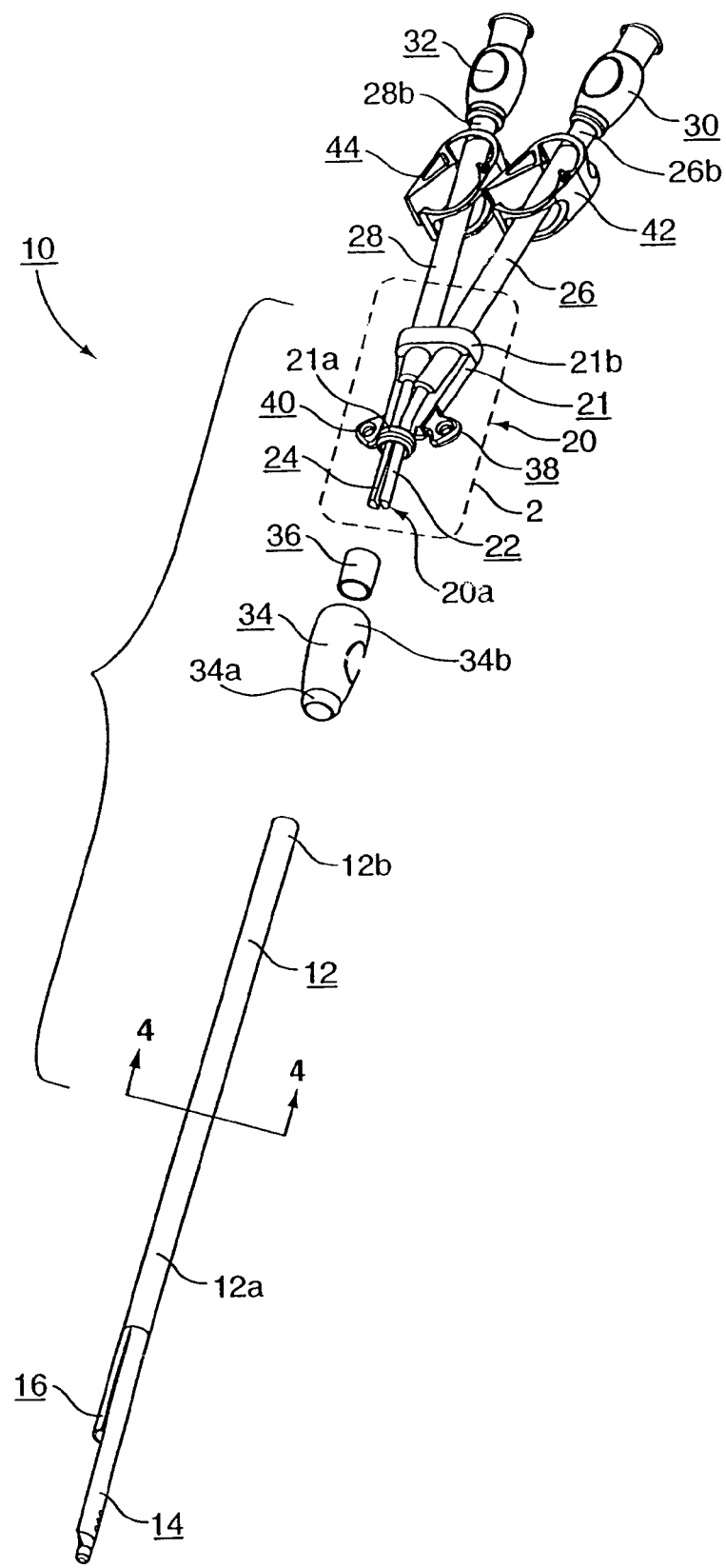
FIG. 1 is an exploded, perspective view of a multi-lumen catheter assembly implanted according to the method of the present invention.

As shown in the Figures, the present invention is a multi-lumen catheter assembly 10 having a selectively attachable hub assembly 20. As shown in FIG. 1, a multi-lumen catheter tube 12 is formed with a proximal portion 12a and a distal portion 12b. The distal portion 12b of the catheter tube 12 is selectively attachable to the proximal portion 20a of the hub assembly 20. In this manner, the hub assembly 20 may be attached to the catheter tube 12 after insertion of the proximal portion 12a of the catheter tube, including tips 14 and 16, into a patient.

Figure 2:
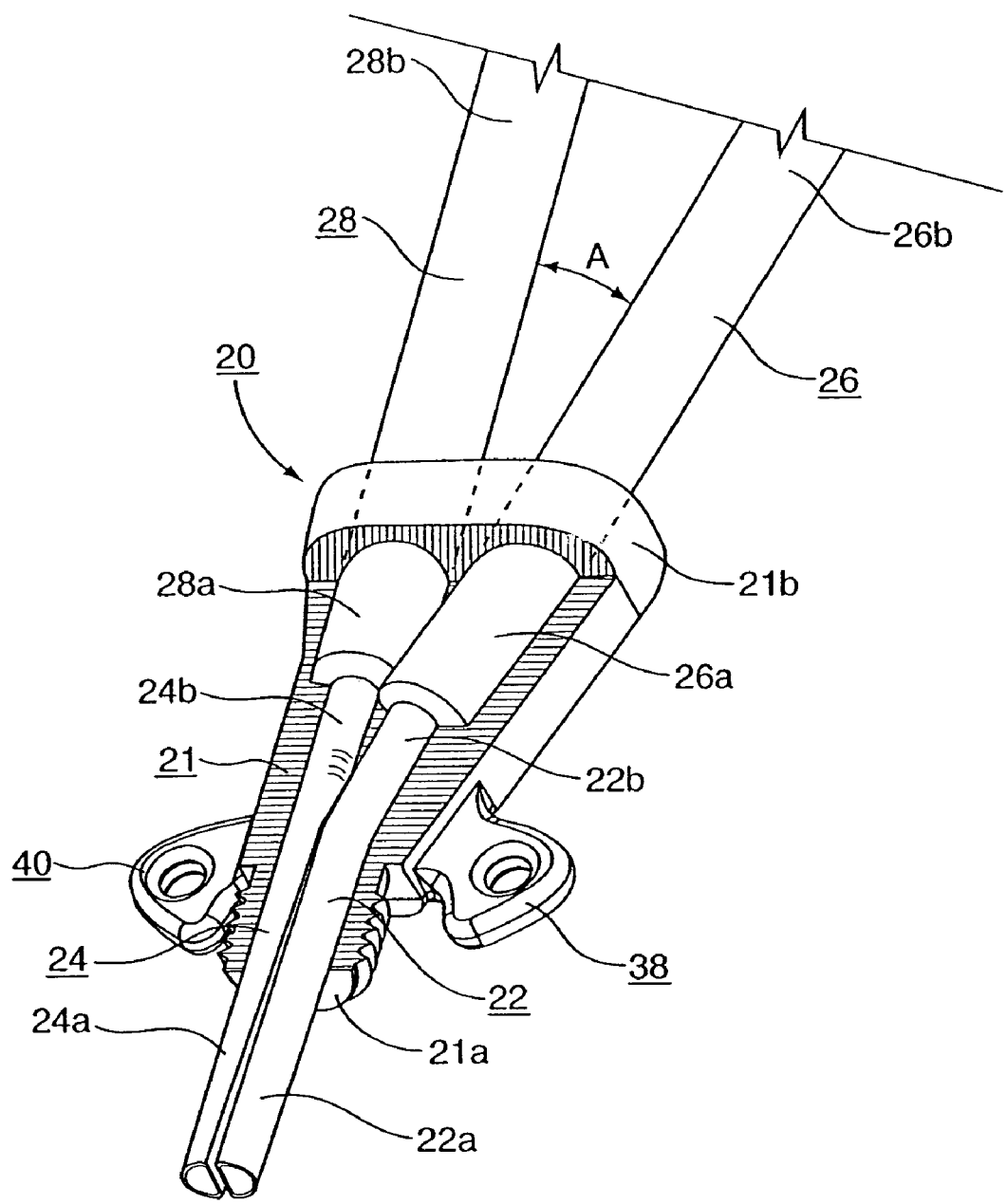
FIG. 2 is an enlarged, exploded, perspective view of a hub assembly of the multi-lumen catheter assembly of FIG. 1, including a first cross-sectional view of the hub body.

As illustrated in FIG. 2, preferably, the hub assembly 20 has a first cannula 22 and a second cannula 24. Each of the cannulae has a proximal portion 22a and 24a, respectively, and a distal portion 22b and 24b, respectively. Further, each cannula 22 and 24 has an associated extension tube, 26 and 28 respectively. Each of the extension tubes 26 and 28 has a proximal portion 26a and 28a, respectively, and a distal portion 26b and 28b, respectively. Each of the extension tubes 26 and 28 are in fluid communication with the first cannula 22 and second cannula 24, respectively, through appropriate connection of respective proximal and distal portions, namely connection of the cannulae distal portions 22b and 24b with extension tube proximal portions 26a and 28a, respectively. While the drawings depict the hub assembly with two cannulae, any appropriate configuration and number of cannulae should be considered within the scope of the present invention.

As shown in FIG. 2, preferably, the hub body 21 is formed to maintain the angle A between the first extension tube 26 and the second extension tube 28 at about 15 degrees. This angle is preferred based upon the necessity for connecting the catheter assembly 10 to the fluid conveying device, e.g., dialysis equipment.

Returning to FIG. 1, the hub assembly 20 further includes a first connector 30 and a second connector 32. The connectors 30, 32 may be luer fittings, as are known in the art. The first connector 30 is securely attached to the distal portion of the first extension tube 26b and the second connector 32 is securely attached to the distal portion of the second extension tube 28b. Each of the connectors 30, 32 preferably is attachable to a fluid conveying device (not shown), such as dialysis equipment, as is known in the art. Thus, the respective cannulae 22 and 24 are in fluid communication with extension tubes 26 and 28, respectively. Therefore, the cannulae 22, 24 provide for respective in-flow and out-flow operation of the fluid conveying device.

Each extension tube 26 and 28 has a clamp, 42 and 44, respectively, for clamping the extension tubes 26 and 28 when the catheter assembly 10 is not connected to a fluid conveying device.

The hub body 21 has two suture wings 38 and 40, which can be used to suture the catheter assembly 10 to the patient to maintain the position of the catheter assembly 10 after insertion into the patient.

Figure 3:
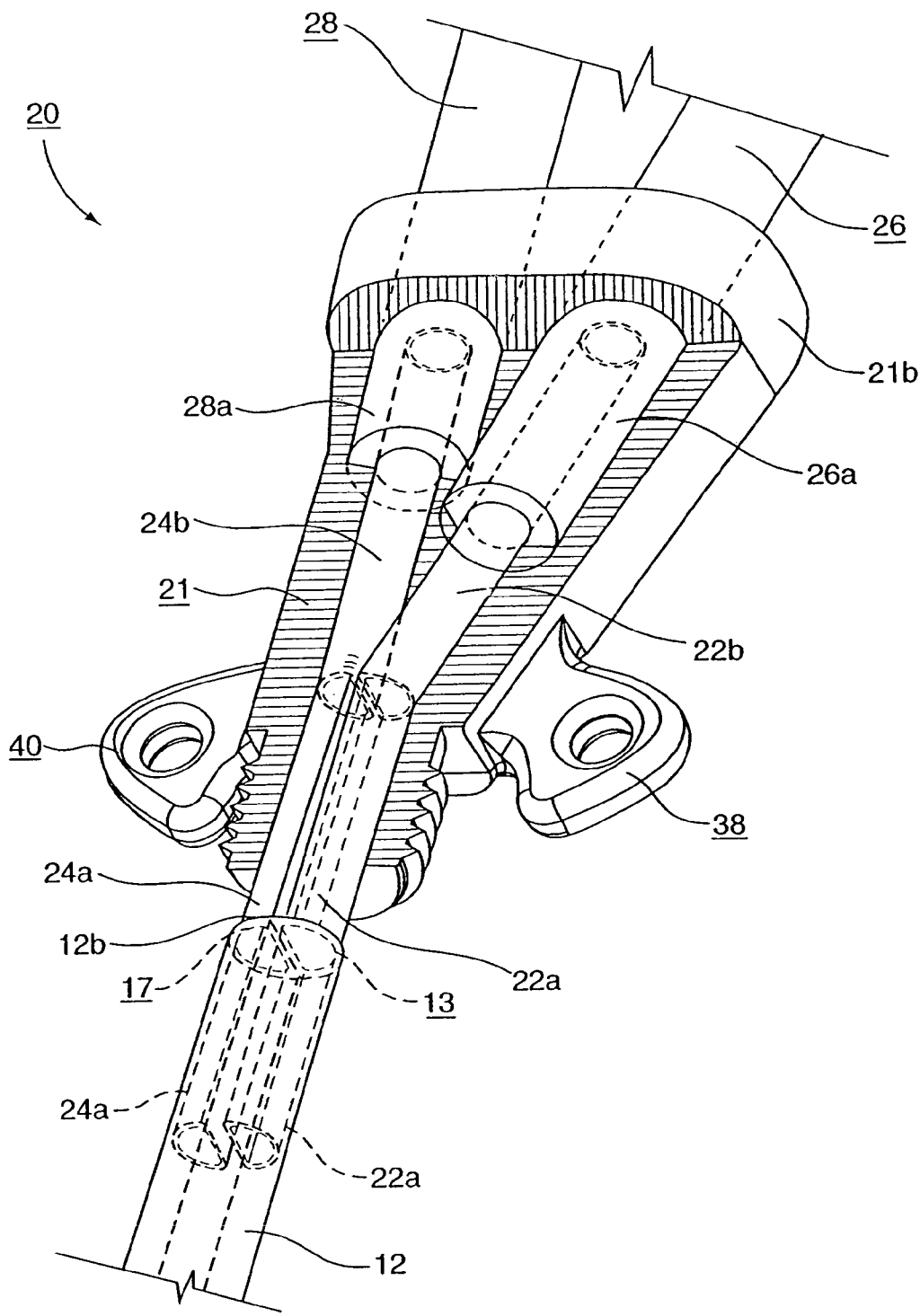
FIG. 3 is an enlarged, exploded, perspective view of the hub assembly and distal portion of the catheter tube of FIG. 1, including the first cross-sectional view of the hub body.

As shown in FIG. 3, the hub assembly 20 preferably is formed such that each proximal end of the cannulae 22a and 24a has a generally D-shaped cross-section. Preferably, the distal portion of each of the cannulae 22b and 24b has a generally O-shaped cross-section. As such, preferably, the proximal portions 26a and 28a of each of the extension tubes 26 and 28a have a generally O-shaped cross-section and are configured to receive the distal portions 22b and 24b of the respective first and second cannulae 22 and 24. The shape and cross-section configuration of the cannulae 22, 24 the extension tubes 26, 28 and the lumens 13, 17 of the catheter tube 12, may be varied, and, thus, the scope of the present invention should not be limited to the above-described preferred configuration.

Preferably, a hub body 21 is formed around the proximal portions of each of the extension tubes and the distal portions of each of the cannulae. As illustrated in FIG. 2, the hub body 21 provides for protection against disconnection of the several connections between cannulae 22, 24 and extension tubes 26, 28. Further, the hub body 21 provides a structure for connection with the catheter tube 12. More specifically, hub body 21 has a proximal portion 21a and a distal portion 21b. As previously mentioned, the hub body 21 is selectively attachable to the distal portion 12b of the catheter tube 12 so as to provide fluid communication between the respective cannulae 22 and 24 (via proximal portions of the cannula 22a and 24a) with the lumens 13 and 17, respectively, of the catheter tube 12, which is discussed in more detail below.

Figure 4:
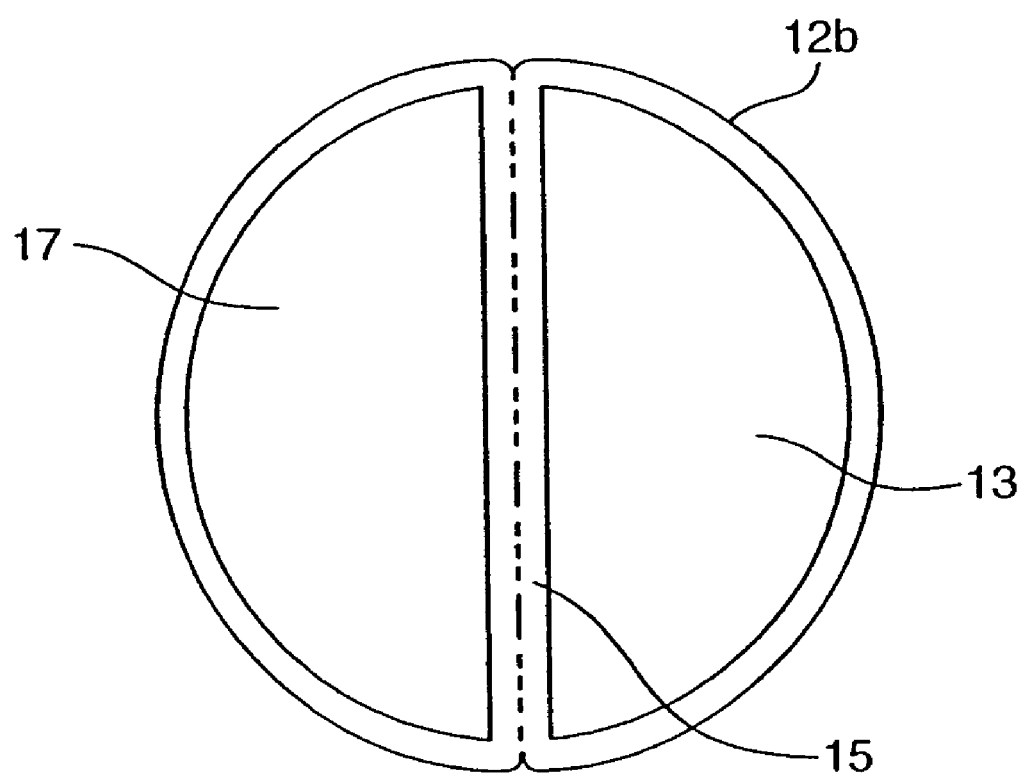
FIG. 4 is a first cross-sectional view of the catheter tube of the multi-lumen catheter of the present invention.
Figure 5:
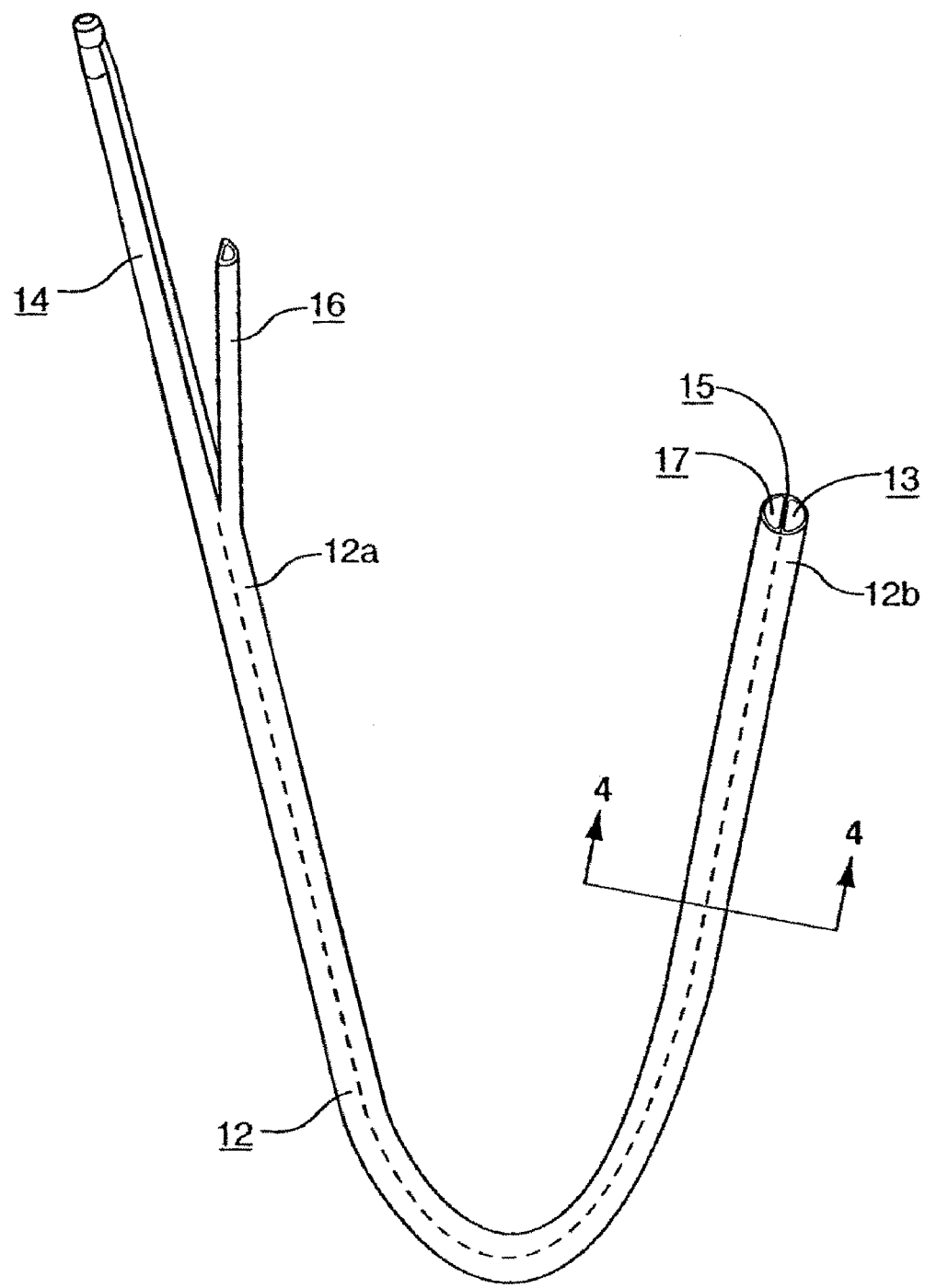
FIG. 5 is an enlarged perspective view of the catheter tube of the present invention.

As shown in FIG. 5, the catheter tube 12 has a first lumen 13 and second lumen 17. Each of the first and second lumen 13, 17 has a generally D-shaped cross-section. A longitudinally extending septum 15 defines each lumen 13, 17 up through the distal portion of the catheter tube 12b, as shown in FIG. 4. Therefore, each lumen 13, 17 connects to a respective cannula 22, 24 for fluid communication therewith.

Preferably, each lumen 13, 17 of the distal portion 12b of the catheter tube 12, and the proximal ends 22a and 24a of the cannulae 22 and 24 are correspondingly marked by an indicator, such as a color, to ensure proper matched correspondence upon connection. To further ensure matched correspondence, preferably tips 14, 16, extension tubes 26, 28 and connectors 30, 32 follow the same marking pattern. Thus, for example, tip 14, the lumen 13, cannula 22, extension tube 26, and connector 30 are marked with a first indicator (e.g., the color blue), while tip 16, lumen 17, cannula 24, extension tube 28, and connector 32 are marked with a second indicator (e.g., the color red). Thus, the first indicator is associated with one of the lumens and a second indicator is associated with the other lumen, such that the first indicator and the second indicator define a correspondence between that lumen and an associated cannula, extension tube, and connector. While the indicator may be a visual indicator such as color, a selectively attachable multi-lumen catheter with any indicator, visual, tactile, or otherwise, should be considered within the scope of the invention.

As described above, the invention is described with a preferred embodiment containing two cannulae and a dual-lumen catheter. The present invention should not be limited, however, to this preferred embodiment and other appropriate configurations should be considered within the scope of the present invention. For example, the catheter tube and corresponding cannulae may be a series of concentric tubes of varying diameter. Alternatively, the assembly 10 may provide a similar configuration to that described hereinabove with three (or more) cannulae and a triple (or more) lumen catheter tube. The preferred embodiment, however, includes two cannulae with a dual-lumen catheter tube.

Preferably, as shown in FIG. 3, the connection between the proximal portions 22a, 24a of the cannulae 22, 24 and the lumens 13 and 17 at the distal portion 12b of the catheter tube 12 is an overlapping fitted connection. However, any other appropriate fastening means, such as detents may be used.

Returning to FIG. 1, an example of a preferred connection between hub body 21 and catheter tube 12 is shown, which includes a connection cover 34 having a proximal portion 34a and a distal portion 34b. Connection cover 34 should fit axially about the distal portion 12b of the catheter tube 12. The distal end 34b of the connection cover 34 is appropriately threaded such that the connection cover 34 is selectively attachable to the threaded portion 21a of the hub body 21 such that the catheter tube 12 is securely attached to the hub assembly 20. For example, as illustrated in FIG. 1, the connection cover 34 may include female threads to selectively receive the male threads 21a formed on hub body 21.

Preferably, the present invention also includes a compression sleeve 36 that fits axially about the distal portion 12b of the catheter tube 12 as well as fitting axially about the combined proximal portions 22a and 24a of the first and second cannulae 22 and 24. Compression sleeve 36 preferably is formed of malleable material so as to provide further compression about the connection between the cannulae 22 and 24 with the multi-lumen catheter tube 12. The connection cover 34 and the compression sleeve 36 together create force to prevent inadvertent separation of the catheter tube 12 from the hub body 21 after insertion of the catheter tube 12 into a patient.

Figure 6:
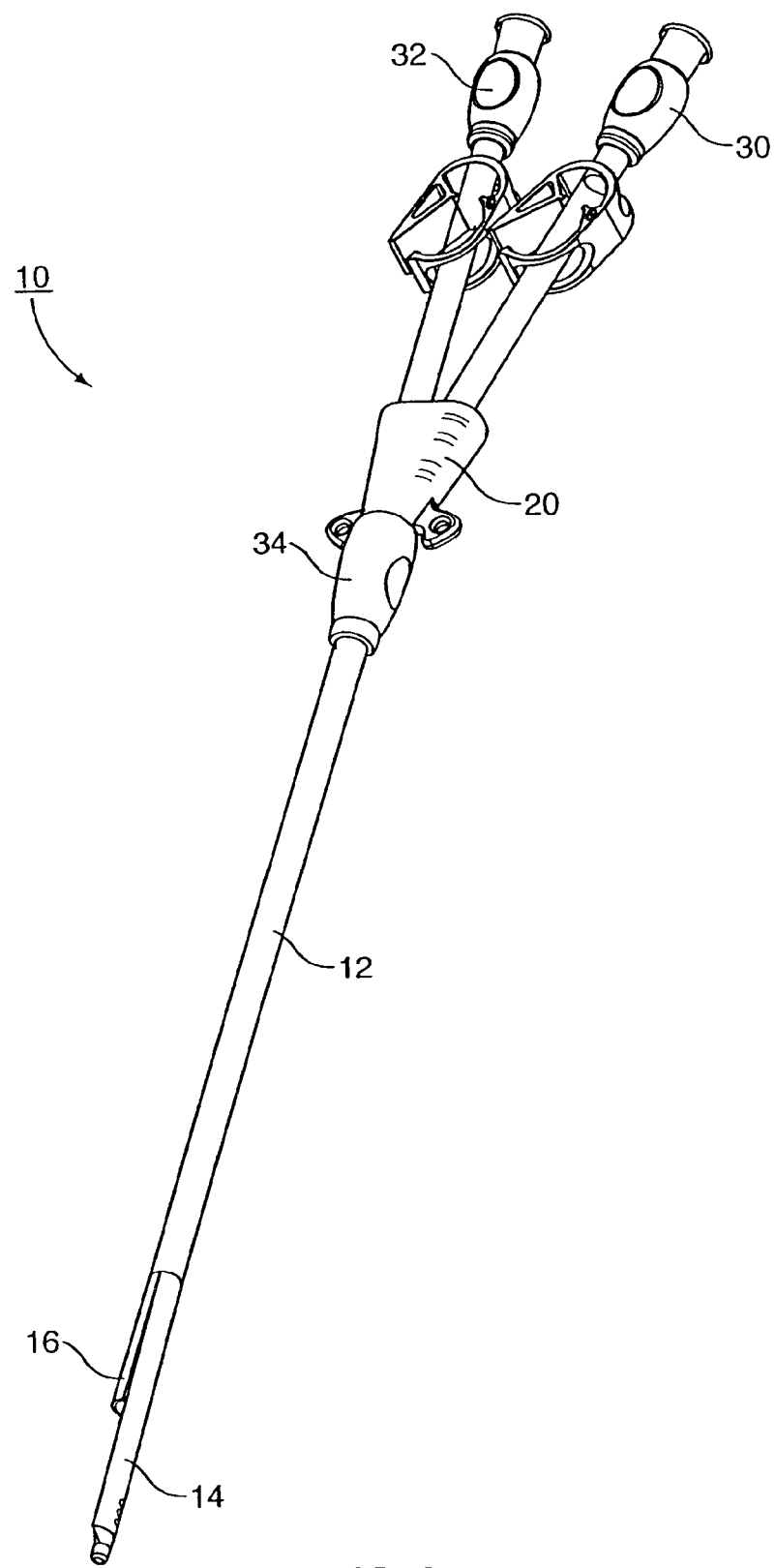
FIG. 6 is a perspective view of an assembled multi-lumen catheter assembly of the present invention.

FIG. 6 shows the catheter assembly 10 of the present invention with the hub assembly 20 attached to the catheter tube 12.

A preferred method for inserting into a patient the catheter assembly 10 of the present invention requires the following: a multi-lumen catheter tube 12 with, preferably, tapered silicone tips 14, 16, and, as are known in the art, an introducer needle, multiple tear away sheath dilator introducers, J-flex guidewires, trocars, lock right adapters with clamps, injection caps, a scalpel, sutures, and adhesive wound dressing. Additionally, the physician should have access to scissors, forceps, needles dish, syringes and gauzes.

Figure 7:
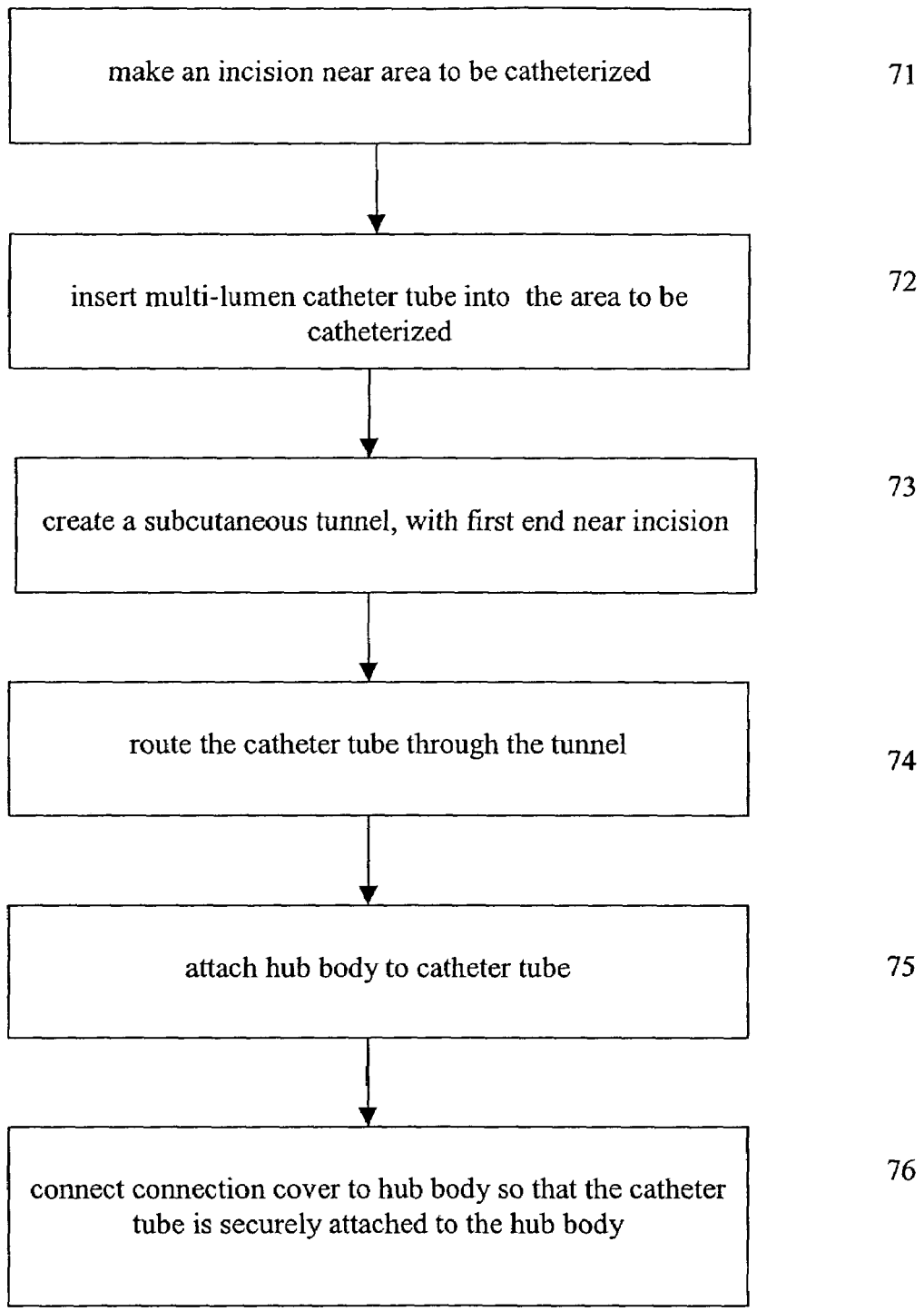
FIG. 7 is a block diagram illustrating a method of inserting a multi-lumen catheter with an attachable hub of the present invention.

FIG. 7 shows a preferred method for insertion of the catheter of the present invention into a patient's jugular vein. The method begins with placing the patient in a position with the patient's head turned to the opposite side of where the jugular vein is to be cannulated. The anatomical landmark for proper insertion is defined by the triangle formed by the lateral edge of the sternal head, the medial edge of the clavicular head of the sternocleidomastoid muscle, and the upper edge of the clavicle.

The patient's neck and a portion of the patient's thorax beneath the clavicle, preferably at least about 20 centimeters (cm), should be appropriately prepared for incision. Thereafter, the patient should be draped and local anesthetic should be administered.

Preferably, a skin wheel should be created, taking care to infiltrate the subcutaneous tissue for about 2 to 3 cm. Next, preferably with an 18-gauge needle attached to a syringe, the physician should identify the internal jugular vein by aspiration and then proceed at an angle while continuing to aspirate with the syringe. Once the internal jugular vein has been located, the preferred method includes detaching the syringe while leaving the needle in place. The needle opening should then be occluded and thereafter the J-flex guidewire should be introduced through the needle and into the internal jugular vein. The guidewire should pass without resistance into the exact position. The needle should be removed, thus leaving the guidewire in place. The guidewire should rest at the junction of the superior vena cava and the right atrium. Appropriate guidewire placement can be confirmed with fluoroscopy.

Next, with a scalpel, the physician should make an incision in the skin that is wide enough for the catheter tube 12 to pass (step 71). A tearaway sheath dilator may be introduced over the guidewire and into the vein far enough to dilate the vessel. After expanding the vein wall, the guidewire may be removed while occluding the dilator opening. A trocar should be screwed onto the catheter tube 12 by turning the trocar clockwise, but not the catheter tube 12. Turning the catheter tube 12 may cause it to kink. The dilator may be removed, leaving the tearaway sheath in place to introduce the catheter tube 12 (step 72), again being careful to occlude the sheath opening. As the catheter tube 12 is fed into the sheath the tearaway sheath may be torn away. Care should be taken that the catheter tube 12 does not back out of the vessel.

Air embolus is avoided by the patient's positioning described above, and also by asking the patient to inhale deeply and then hold their breath. At this point, fluoroscopy should be performed to confirm catheter tube 12 placement. The tip 14 of the venus catheter should reach the opening of the right atrium and the tip 16 of the arterial catheter should be approximately 4 cm higher. As described above, proper positioning is important. Positioning, as described, is believed to prevent blood recirculation during hemodialysis.

Next, a tunnel, of about 8 to 10 cm, should be created (step 73) in a caudal and internal direction by means of the tunneler, which may be shaped to physician preference. The catheter tube 12 should be gently pulled through the tunnel (step 74) until the loop at the original puncture site is gone. When correctly inserted, the catheter tube 12 should rest over the clavicle. Care should be taken to avoid excessive force, as this may cause the catheter tube 12 to separate from the tunnel. Preferably, the method includes surveying this area to ensure there are no kinks in the catheter tube 12 and there is a smooth turn.

Next, while pinching the distal portion 12b of the catheter tube 12, the hub assembly 20 is attached to the catheter tube 12 (step 75). The connector 34 is backfit over the catheter tube 12. Next, the compression sleeve 36 is backfit over the catheter tube 12. The proximal portions 22a, 24a of cannulae 22, 24 are inserted into lumens 13 and 17, respectively, creating a friction fit. Preferably, the cannulae 22, 24, or the corresponding extension tubes 26, 28 or the corresponding connectors 30, 32 are marked so that the cannulae 22, 24 are inserted into the correct lumens 13, 17.

After backfiting the connector cover 34 and the compression sleeve 36 over the catheter tube 12, the compression sleeve 36 is slid into a position that is approximately adjacent to the threaded portion 21a of the hub body 21. Finally, the connector cover 34 is attached to the hub body 21 (step 76) by turning the connector cover 34 so that the female threaded portion of the connector cover 34 receives the male threaded portion 21a of the hub body 21 thereby creating a secure attachment of the hub assembly 20 to the catheter tube 12. Clamps 42, 44 may be used with extension tubes 26, 28.

The extension tubes 26, 28 should be filled with 3 to 4 cc of 5000 units of heperinized saline, clamped, and attached with the injection cap. X-rays should again be performed to reconfirm placement. The small incision is closed with sutures. The patient is now ready for dialysis.

As can be appreciated by those skilled in the art, variations in the sequence of the steps are within the scope of the invention. For example, the subcutaneous tunnel could be created prior to inserting the catheter into the area to be catheterized. Also, the incision near the area to be catheterized can be made prior to routing the catheter tube through the tunnel, and the catheter tube can be routed through the subcutaneous tunnel prior to inserting the catheter in the area to be catheterized.

Although specific embodiments of the present invention have been illustrated and described in detail, it is to be expressly understood that the invention is not limited thereto. The above detailed description of the embodiment is provided for example only and should not be construed as constituting any limitation of the invention. Modifications will be obvious to those skilled in the art, and all modifications that do not depart from the spirit of the invention are intended to be included within the scope of the appended claims. Also, as is known in the art, the terms "distal" and "proximal" are relative terms with respect to a point of reference. For purposes of the foregoing detailed description of the invention, the point of reference is the area to be catheterized.

The invention claimed is:

1. A method for inserting a multi-lumen hemodialysis catheter assembly into an area to be catheterized, the multi-lumen hemodialysis catheter assembly having (a) a multi-lumen catheter tube having a distal portion and a proximal portion, and (b) extension tubes each having a proximal end and a distal end, the proximal end selectively attachable to the distal portion of the multi-lumen catheter tube, the method comprising the steps of:
   making an insertion incision near the area to be catheterized;
   inserting the proximal portion of the multi-lumen catheter tube into the area to be catheterized;
   creating a subcutaneous tunnel having a first end and a second end, wherein the first end of the subcutaneous tunnel is near said insertion incision;
   routing the distal portion of the catheter tube through the subcutaneous tunnel beginning at the first end and exiting through the second end of the subcutaneous tunnel;
   subsequent to routing the distal portion of the catheter tube through the subcutaneous tunnel, attaching the proximal end of each extension tube to the distal portion of the catheter tube; and
   attaching the distal end of each extension tube to a hemodialysis fluid circulation device.

2. The method of claim 1, the catheter tube having at least a first lumen and a second lumen, the proximal end of each extension tube comprising a cannula, each of the cannula having a proximal portion and a distal portion, wherein the step of attaching the proximal end of each extension tube to the distal portion of the catheter tube further comprising of the step of:
   inserting the proximal portion of each cannula into each of the first lumen and second lumen at the distal portion of the catheter tube to create fluid communication between each cannula and the first lumen and the second lumen.

3. The method of claim 2, the first lumen having a first indicator associated therewith, and the second lumen having a second indicator associated therewith, wherein the step of inserting the cannula into the lumens further comprising the steps of:
   matching the first indicator associated with the first lumen with an indicator associated with one of the cannula; and
   matching the second indicator associated with the second lumen with an indicator associated with the other cannula.

4. The method of claim 1 further comprising of the steps of:
   engaging a clamp engaged with each extension tube to prevent fluid flow therethrough; and
   disengaging the clamp to allow fluid from through each extension tube.

5. The method of claim 1, wherein the step of attaching the proximal end of each extension tube to the distal portion of the catheter tube is preceded by:
   gripping the proximal end of each extension tube by a gripping portion sized such that fingers may grip and manipulate the proximal end of the extension tubes.

6. The method of claim 1, a connector attached to the distal end of each connection tube to ease the step of attaching the distal end of each extension tube to a hemodialysis fluid circulation device.

7. A method for inserting a multi-lumen hemodialysis catheter assembly into an area to be catheterized, wherein the multi-lumen hemodialysis catheter assembly is comprised of (a) a multi-lumen catheter tube with a distal portion and a proximal portion, the catheter tube having a first lumen and a second lumen, (b) a first and second extension tube each having at a proximal end thereof a cannula, each of the cannula having a proximal portion and a distal portion, the method comprising the steps of:
   making an insertion incision near the area to be catheterized;
   inserting the proximal portion of the multi-lumen catheter tube into the area to be catheterized;
   creating a subcutaneous tunnel having a first end and a second end, wherein the first end of the subcutaneous tunnel is near the insertion incision;
   routing the distal portion of the catheter tube through the subcutaneous tunnel beginning at the first end and exiting through the second end of the subcutaneous tunnel;
   subsequent to routing the distal portion of the catheter tube through the subcutaneous tunnel, attaching the proximal portion of each cannula to the distal portion of the catheter tube; and
   attaching a distal end of each extension tube to a hemodialysis fluid circulation device.

8. The method of claim 7 further comprising of the steps of:

engaging a clamp disposed about the extension tube to prevent fluid flow therethrough; and disengaging the clamp to allow fluid flow through the extension tube.

9. The method of claim 7, wherein the step of attaching the cannula of each extension tube to the distal portion of the catheter tube is preceded by:
gripping the first end of each extension tube by a gripping portion sized such that a fingers may grip and manipulate the cannula of each extension tubes.

10. The method of claim 7, further comprising a connector attached to each extension tube distal end.

11. The method of claim 7 wherein the step of attaching the cannula to the catheter tube further comprising of the steps of:
inserting the proximal portion of the cannula of the first attachable extension tube into the first lumen of the distal portion of the catheter tube, and inserting the proximal portion of the cannula of the second attachable extension tube into the second lumen of the distal portion of the catheter tube, to create fluid communication between the cannula of the first extension tube and the first lumen and the cannula of the second extension tube and the second lumen.

12. A method for inserting a multi-lumen hemodialysis catheter assembly into an area to be catheterized, wherein the multi-lumen hemodialysis catheter assembly is comprised of
(a) a multi-lumen catheter tube with a distal portion and a proximal portion, the catheter tube having at least a first lumen and a second lumen,
(b) an attachable hub assembly, the hub assembly having
(i) a hub body being formed about a first cannula and a second cannula, each cannula having a proximal portion and a distal portion,
(ii) a first extension tube attached to the distal portion of the first cannula in fluid communication therewith and a second extension tube attached to the distal portion of the second cannula in fluid communication therewith, the first lumen and the first extension tube having a first indicator associated therewith, the second lumen and the second extension tube having a second indicator associated therewith, the second indicator being easily distinguishable from the first indicator;
the method comprising the steps of:
making an insertion incision near the area to be catheterized;
inserting the proximal portion of the multi-lumen catheter tube into the area to be catheterized;
creating a subcutaneous tunnel having a first end and a second end, wherein the first end of the subcutaneous tunnel is near the insertion incision;
routing the distal portion of the catheter tube through the subcutaneous tunnel beginning at the first end and exiting through the second end of the subcutaneous tunnel;
matching the indicator associated with each lumen with the corresponding indicator associated with each extension tube; and
attaching the proximal portion of the cannula to the distal portion of the catheter tube.

13. The method of claim 12 further comprising of the steps of:
engaging a clamp disposed about the extension tube to prevent fluid flow therethrough; and
disengaging the clamp to allow fluid flow through the extension tube.

14. The method of claim 12, wherein the step of attaching the proximal portion of each cannula to the distal portion of the catheter tube is preceded by the step of:
gripping the first end of each extension tube by a gripping portion sized such that a typical persons finger could grip and easily manipulate the cannula of each extension tube.

15. The method of claim 12, wherein each extension tube has a distal end, the step of attaching the proximal portion of each cannula to the distal portion of the catheter tube is followed by the step of:
connecting the distal end of each extension tube to a fluid circulation device.

* * * * *